United States Patent [19]
Goust et al.

[11] 4,001,080
[45] Jan. 4, 1977

[54] PRODUCTION OF IMMUNOLOGICAL MATERIALS

[75] Inventors: Jean Michel Goust; Robert Louis Moulias, both of Paris, France

[73] Assignee: Piktor Limited, Paris, France

[22] Filed: May 5, 1975

[21] Appl. No.: 574,256

Related U.S. Application Data

[63] Continuation-in-part of Ser. No. 407,192, Oct. 17, 1973, abandoned.

[30] Foreign Application Priority Data

Oct. 20, 1972 United Kingdom ............ 48486/72

[52] U.S. Cl. ................................................ 195/1.8
[51] Int. Cl.$^2$ ......................................... C12K 9/00
[58] Field of Search ..................................... 195/1.8

[56] References Cited
OTHER PUBLICATIONS

Dixon et al., Advances in Immunology, vol. 11 (1969) pp. 234 to 244.

*Primary Examiner*—Sam Rosen
*Attorney, Agent, or Firm*—Marn & Jangarathis

[57] ABSTRACT

Transfer factor is produced by in vitro culture of lymphoblastoid cell lines after induction with transfer factor, which may be mono- or poly- specific. The produced transfer factor is then extracted from the lymphoblastoid cell lines.

3 Claims, No Drawings

PRODUCTION OF IMMUNOLOGICAL MATERIALS

This Application is a continuation-in-part of U.S. Ser. No. 407,192 filed 17 Oct. 1973, now abandoned.

BACKGROUND OF THE INVENTION

It is well known that part of the immune reaction in man and other animals is provided by antibodies: these are proteins which form part of the immunoglobulins produced by the lymphoid cells and which circulate in the blood. Antibodies combine chemically with antigens so as to neutralize them; however, it has been realized that, in many conditions, the antibodies do not provide the necessary degree of immunity and increasingly the importance is being recognized of the part played by the lymphocytes in providing cellular immunity. The lymphocytes also carry the immunological memory, and they provide a natural defence against viral infections and against the growth of neoplasms. Although some medical conditions are characterized by a deficiency of cellular immunity, treatment by transfusion of lymphocytes is unsatisfactory for two reasons: (a) a suitable donor is needed; and (b) the transfused lymphocytes can produce a transplant reaction in the host.

The presence in lymphocytes of a substance now commonly referred to as "transfer factor," and the role of this substance as carrier of the cellular immune memory, was first demonstrated by H. S. Lawrence [Lawrence H. S., "The transfer in humans of delayed skin sensitivity to streptococcal M substance and to tuberculin with disrupted leucocytes" J. Clin. Invest (1955) 34, 219–30; Lawrence H. S., Al Askari S., and David J., "Transfer of immunological information in humans with dialysates of leucocyte extracts," Trans. As. Amer. Physicians (1963) 76, 84–91; Lawrence H. S., "Transfer factor and cellular immune deficiency diseases," New Engl. J. Med. (1970) 283, 411–9; and Lawrence H. S., "Transfer factor" Advances in Immunology (1969), 11, 195–266]. It has since been demonstrated that the substance referred to as "transfer factor" is, in fact, a mixture of substances (which may be defined by chemical properties, spectrophotometric profile and, mainly, the biological property of transferring cellular immunity against one or a plurality of antigens) and is, therefore, more properly referred to as "transfer factors." This substance, which has been found in man and other primates, can transfer only cellular immune responses, and not the ability to secrete anitibodies. After contact with an antigen, the lymphocyte memory will contain transfer factors, which are currently believed to be specific to the class of antigens to which belongs the antigen with which the lymphocyte was contacted. Thus, transfer factors are specific to a class of antigens and exclusively to cellular immunity. However, the lymphocytes of a normal adult will contain transfer factors corresponding to each of the viral, bacterial or other antigens with which he has been in contact, so that dialysates of leucocyte extracts will contain a polyspecific transfer factor mixture.

Dialysis of transfer factors will divide them into dialysable transfer factor and non-dialysable transfer factor. Available evidence shows that dialysable transfer factor appears to be a small molecule, whose approximate molecular weight is estimated to be in the range of about 7,000; in fact, dialysable transfer factor itself would appear to be a mixture of molecules having various molecular weights, the majority being close to about 7,000 and the numbers of molecules with molecular weights substantially below about 4,000 or substantially above about 10,000 being negligible. Dialysable transfer factor appears to contain a ribonucleotide, but is not destroyed by ribonuclease. It has been shown to be stable for indefinite periods when lyophilized and kept at −20° C. On the hand, nondialysable transfer factor is a larger molecule and has been characterized as RNA having a molecular weight greater than 30,000; both are not species-specific but are specific to an antigen class and are also specific to the transfer of cellular immunity.

Since dialysable transfer factor is not antigenic, that is to say that it cannot induce an immune reaction, its therapeutic administration would be preferable to the transfusion of lymphocytes. Indeed, experimental treatment with dialysable transfer factor has already proven successful in remedying deficiencies of cellular immunity and in obtaining amelioration of various diseases; thus, it has been used with indications of success in the treatment of subacute sclerosing panencephalitis, systemic candidiasis, malignant melanoma, breast cancer, measles and chickenpox, although it will be appreciated that this is by no means an exhaustive list of the diseases against which such treatment is effective. However, the prior art methods of producing transfer factors, which rely on donor blood as the starting material, do not permit transfer factors to be produced satisfactory for use as therapeutic agents: the production of any pure substance from whole blood is a tedious operation, requiring the preliminary separation of the lymphoid cells from a large volume of selected human blood.

It has been proposed to culture lymphocyte cells in vitro [Lawrence H. S., "Transfer factor" Advances in Immunology (1969) 11, 195–266] but this is primarily for the purpose of maintaining the lymphocytes alive and the transfer factor in usable condition after the lymphocyte cells have been removed from the donor and also to enable experiments to be carried out on those cells which could not conveniently or ethically be carried out in vivo in humans. Also, Jachertz in British Patent No. 1,229,888 discloses that a material he terms "informationally active RNA" can be synthesized in vitro and the product may be used as a "vaccine." The "informationally active RNA" of Jachertz is said to be produced by various "immunologically competent cells," including human and monkey leukocytes; Jachertz discloses that the immunologically competent cells may be cultured before the RNA is extracted therefrom. However, the cell culture is only carried out for a short time (5–60 minutes) and effectively does no more than maintain the cells alive: the process could not form the basis for commercial large-scale production of transfer factor. Furthermore the non-dialysable "informationally active RNA" is not the same product as transfer factor.

Thus, none of the prior art methods lends itself to the large-scale production of transfer factor under standardized, reproducible conditions. Moreover, because they use donor blood, these methods can only produce transfer factors which are specific to those classes of antigen with which the donor has been in contact; they cannot be modified to produce a particular antigen-specific transfer factor at will, except by choice of an appropriate blood donor.

Lymphocytes and other related cells cannot be maintained in cell culture for substantial periods of time without modification. It is, however, well-known that such cells may be transformed in such a way that they can be maintained in cell culture indefinitely. However, in the course of this modification, substantial changes in the character and properties of the cells are observed; the resulting cells are termed "lymphoblastoid cells." Although derived from lymphocytes, they share very few of the properties of native lymphocytes and are regarded by those skilled in the art as a *totally different type of cell*. We have now discovered that cultures of blastoides can be artificially induced to produce transfer factor, even if transfer factor was not previously present in the cells.

It is, therefore, one of the principal objects of Applicants invention to provide a process for producing transfer factor which *does not rely upon donor blood* and which can be used for the production at will of large quantities of any particular antigen-specific transfer factors desired.

It is a further and more specific object of the invention to provide a process in which lymphoblastoid cells are induced to produce transfer factor.

SUMMARY OF THE INVENTION

We have now suprisingly discovered that lymphoblastoid cells can be induced to produce a particular antigen-specific transfer factor or a desired mixture of transfer factors by culturing the cells in the presence of the specific transfer factor or factors. On the basis of this discovery, the present invention makes it possible to produce transfer factors in large quantities by a standardized, reproducible method, and to produce particular antigen-specific transfer factors at will.

Broadly, therefore, the invention provides a process for the in vitro production of transfer factor comprising: culturing in vitro at least one strain of lymphoblastoid cells in the presence of added transfer factor to propagate the cells and induce the production of transfer factor by them; and extracting the produced transfer factor. The transfer factor used may be dialysable and/or non-dialysable transfer factor. Once the cell cultures have been induced by this process, the transfer factors they produce may be used in the same way and with the same indications as the transfer factors which served to induce the culture.

Certain cells will release some transfer factor into the supernatant of the culture medium and, where such cells are employed, the transfer factor may be extracted from the supernatant. Alternatively, or in addition, the transfer factor may be extracted from the lymphoblastoid cells themselves. In either case, the extraction of the transfer factor and the purification of the extract can be carried out by per se known techniques, to produce a pure preparation of transfer factor.

DESCRIPTION OF PREFERRED EMBODIMENTS

The process of the present invention induces lymphoblastoid cells to produce transfer factor by contacting the lymphoblastoid cells with a desired transfer factor or transfer factors. The lymphoblastoid cells may be prepared by modification of lymphocytes using known techniques, e.g. as described by G. E. Moore and K. Ulrich [J. Surg. Res. 5, 270–282 (1965)] or G. E. Moore, R. E. Gerner and H. Addison-Franklin [J. Amer. Med. Assoc. 199, 87–92 (1967)]. Another technique consists in the repeated contact of cultured lymphocytes with small doses of phytohaemagglutinin (P.H.A.). By means of these techniques, lymphoblastoid cell lines are produced and are suitably maintained in culture at a concentration of from $2 \times 10^5$ to $1 \times 10^6$ cells per millilitre. Lymphoblastoid cells obtained by modification of lymphocytes derived either from man or from animals other than man (especially the other primates) may be employed in the process of the present invention and, in view of the substantial modification to which lymphocytes are subjected to produce lymphoblastoid cells, the ultimate origin of the lymphoblastoid cells is not critical to the process of the invention. It is possible, for example, to use cultures of lymphoblastoid cells produced by modification of lymphocytes derived from animals other than man and induce them to produce human transfer factor and, of course, the converse is also possible.

The production of a particular transfer factor is, in accordance with the present invention, induced by the presence in the culture medium of the appropriate specific transfer factor during at least part of the culture period. The transfer factor used as the inducer may be any desired transfer factor and need not necessarily be related to the lymphoblastoid cells employed; thus, it is possible to use lymphoblastoid cells derived from monkey lymphoid cells and induce them with human transfer factor to produce more transfer factor, which is effective in human beings.

After the desired period of cultivation, the transfer factor produced may be extracted from the cultured cells by techniques well-known to those skilled in the art. Thus, the cells should first be disrupted, which may be achieved by repeated freezing and thawing or by treatment with a chemical cell-disrupting agent, e.g. Triton-X100. In general, the use of a chemical cell-disrupting agent is preferred, since only small amounts need be used and the process is extremely fast, e.g. of the order of about 5 minutes or less with Triton-X100, although longer periods may be optimal with other chemical cell disrupting agents.

Alternatively, or in addition, where the cells are of the type which release transfer factor into the supernatant, the produced transfer factor may be extracted from the supernatant by procedures well-known for extracting other cell products. For example, the supernatant may be passed through a semi-permeable membrane which does not allow the passage of molecules of molecular weight more than 10,000. The semi-permeable membrane used is preferably a Diaflow membrane.

The product obtained by the process of the present invention can be shown to be transfer factor by chemical and spectroscopic tests. For example, it can be shown that the ultra-violet spectrum of the substance produced by the process of the present invention is the same as that of transfer factor extracted from peripheral blood lymphocytes; both exhibit a UV absorption minimum at 242 nm and a maximum at 258 nm.

The invention is more fully described by reference to the following Examples, which are chosen from the many experiments which were conducted to define the invention and which are intended to be representative of preferred embodiments of the invention and not restrictive of the scope of the invention.

EXAMPLE 1

In this Example, lymphoblastoid cells were incubated throughout with a constant concentration of transfer factor. In separate experiments, transfer factor equivalent to $10^2$, $10^3$ or $10^4$ cells was added to 200 millilitres of culture containing $4 \times 10^5$ cells per millilitre. The cells were allowed to grow until they reached a concentration of $10^6$ per millilitre, after which fresh culture medium containing the chosen concentration of transfer factor was added, diluting the cell concentration back to $4 \times 10^5$ cells per millilitre. This culture procedure was continued until sufficient cells were obtained. The transfer factor was then extracted by per se conventional techniques, as described above.

EXAMPLE 2

In separate experiments, lymphoblastoid cells were incubated with transfer factor in amounts equivalent to $10^3$ or $10^4$ cells. The cells were allowed to grow for about 2 days, after which medium which did not contain transfer factor was added to dilute the cells. About 3 days later, the cells were harvested and the transfer factor was extracted therefrom by the conventional techniques described above.

EXAMPLE 3

Preparation of cell culture:

Peripheral blood lymphocytes from an apparently healthy donor were cultured in the presence of P.H.A. by a modification of the techniques of G. E. Moore, E. Ito, K. Ulrich, and A. A. Sandberg [Cancer 19, 713 (1966)]. The culture medium was RPMI – 1640 medium supplemented with 10% fetal calf serum (Gibco:Bio-cult, Glasgow) containing 15 mg/litre gentamycin sulphate, and the cells were grown in suspension cultures.

Preparation of transfer factor inducer:

Peripheral blood lymphocyte dialysable transfer factor was prepared by a modification of the technique described by H. S. Lawrence [B. R. Bloom and P. R. Glade (Eds.) "In Vitro Methods in Cell-Mediated Immunity," New York, Academic Press (1971) pages 95 and 531]. The cells were disrupted by 10 freeze-thaw cycles and then centrifuged at 40,000G for 60 minutes. The supernatant was dialysed against a 0.005M aqueous solution of sodium chloride at 4° C, and the dialysate was then lyophilized.

Induction procedure:

Cells cultured as described above (hereinafter referred to as "BF" cells) were suspended in the culture medium described above at a concentration of $4 - 5 \times 10^5$ cells per millilitre and sterilized peripheral blood transfer factor, prepared as described above, was added. The amount of cell culture used was about 275 millilitres and the peripheral blood transfer factor was added in an amount corresponding to a ribose content of about 15 μg per $10^8$ cells. The cells were then grown, fresh medium being added as required. Samples of approximately $10^8$ cells were taken each week for 5 weeks.

Transfer Factor Extraction:

Each sample of cultured cells was lyophilized and stored at −20° C prior to extraction of transfer factor. The lyophilized cells were then suspended in water for injections and ruptured by freezing, followed by thawing at 37° C, repeated five times. The product was then centrifuged for 20–30 minutes at 250G. The supernatant liquid was then centrifuged for 1 hour at 20,000G and 4° C; the product was then placed in a high flow rate pressure ultrafiltration apparatus (Amicon DC2), using successively "Diafiber" filter cartridges XM50 (which retain substances with a molecular weight above 50,000) and then PM10 cartridges (which retain substances with a molecular weight above 10,000). The dialysate was then concentrated on an Amicon UM2 membrane (which retains substances with a molecular weight above 1,000 ). This final concentrate was then lyophilized.

The identity of the product with transfer factor was demonstrated by skin tests on rats and by in vitro tests on nonresponding lymphocytes (Migration Inhibition Test, rosette formation, lymphocyte stimulation) and in vivo tests on clinical efficiency.

EXAMPLE 4

The procedure described in Example 3 was repeated, except that the cells initially used were established from non-malignant lymphatic tissue (tonsils); the resulting lymphoblastoid cell line is herein referred to as line BF. As in Example 3, transfer factor was obtained.

EXAMPLE 5

Lymphoblastoid cell lines B18, B12 and BF were cultured and induced with transfer factor, as described above. $5 \times 10^8$, $6.9 \times 10^7$, and $7 \times 10^7$ cells, respectively, were then harvested from the cultures, lyophilized and stored at −20° C. The lyophilized cells were re-suspended in water and ruptured by freezing followed by thawing at 37° C (repeated five times). Each cell sample was centrifuged separately for 20–30 minutes at 150–250G. The supernatant liquid was then centrifuged for 1 hour at 20,000G at 4° C in a Sorvall RC2B centrifuge. The product obtained from each cell sample was then placed in a high flow rate pressure ultrafiltration apparatus (Amicon DC2), using successively "Diafiber" filter cartridges XM50 (retaining substances with a molecular weight above 50,000) and then PM10 (retaining substances with a molecular weight above 10,000). The dialysate, consisting of the supernatant liquid derived from the ruptured lymphoblastoid cells, diluted 10 times with 0.05M physiological saline, was concentrated on an Amicon UM2 membrane (which retains substances with a molecular weight about 1,000). This final concentrate, having a volume of from 10 to 20 millilitres in the three respective cases, was lyophilized.

EXAMPLE 6

Human peripheral blood lymphocytes were put into 10 millilitres of a conventional nutrient medium at a concentration of about $10^6$ cells per millilitre. P.H.A. was then added in an amount of about 0.1 μg/ml (equivalent to 0.1 μg per $10^6$ cells). Every 2 days, half of the old nutrient medium was eliminated and fresh medium containing P.H.A. (0.1 μg/ml) was supplied. This procedure was continued until the lymphocytes had been sufficiently modified to establish a lymphoblastoid cell line capable of continuous replication without outside stimulation. This normally took from 6 to 12 weeks, the precise time being determined empirically.

The lymphoblastoid cell line so produced was then diluted with fresh nutrient medium to produce 200 millilitres of culture containing $4 \times 10^5$ cells per millilitre. An amount of antigen-specific transfer factor equivalent to $10^3$ cells was then added to this culture and the cells were allowed to grow until they reached a concentration of $10^6$ cells per millilitre. Fresh nutrient medium containing transfer factor in amount equivalent to $10^3$ cells was then added to dilute the cell concentration back to $4 \times 10^5$ cells per millilitre.

The cells were then harvested, lyophilized and stored at $-20°$ C in readiness for extraction of transfer factor. The lyophilized cells were resuspended in water for injections and ruptured by treatment for 5 minutes with Triton-X100 in a concentration of 0.5% in a buffer. The supernatant liquid was then centrifuged for 1 hour at 20,000G and 4° C in a Sorvall RC2B centrifuge. The supernatant from this centrifugation was then placed in a high flow rate pressure ultrafiltration apparatus (Amicon DC2) using successively "Diafiber" filter cartridges XM50 and then PM10. The dialysate, consisting of the supernatant liquid derived from the ruptured lymphoblastoid cells, diluted 10 times with 0.05M physiological saline, was concentrated on an Amicon UM2 membrane and then lyophilized.

EXAMPLE 7

A culture of lymphoblastoid cell line BF was primed with transfer factor obtained from peripheral human blood and then cultured in a medium containing phenol red. For control purposes, a similar culture was prepared without priming with the transfer factor. The supernatant from each culture was dialysed using a Diafiber H1 DP10 membrane (which retains substances of molecular weight above 10,000). The dialysate contained phenol red and any dialysable transfer factor released from the cells. Dialysis was discontinued when all the phenol red had passed into the dialysate, which was then freeze-dried.

The dialysate from each culture was subjected to physico-chemical evaluation to determine whether transfer factor was present. This was carried out by chromatographing the dialysate on a column of Biogel P10 (which retains substances having molecular weights from 10,000 to 2,000) previously equilibrated with tris(hydroxymethyl)aminomethane. The various fractions present in the eluate were identified by measurement of optical density. Transfer factor obtained by the process of the invention, like that obtained from human blood, exhibits an absorption band at 265 m $\mu$ characteristic of the presence of nucleic acids. Any fraction of the eluate apparently containing transfer factor was collected and tested for ribonucleotides by the orcinol reaction [Z. Dische in E. Chargaff and J. N. Davidson (Eds.) "The Nucleic Acids," New York, Academic Press (1955)] and for protein by the method of O. H. Lowry et al [J. Biol. Chem. 193, 265 (1961)].

The dialysate was an eluate fraction containing a material exhibiting an absorption band at 265 m $\mu$. The fraction was present in the same portion of the eluate as a known eluate fraction containing transfer factor extracted from induced cells themselves (e.g. as described in Example 3). The fraction had a ribonucleotide: protein ratio comparable with that of the known eluate fraction and thus was shown to contain transfer factor which was chemically very similar to the transfer factor extracted from induced cells.

Several different types of tests can be used to show that the extracts of transfer factor obtained in the above Examples contain transfer factor having essentially the same properties as transfer factor isolated from human blood. Firstly, this can be demonstrated in vitro, using tests measuring MIF secretion, especially the Leucocyte Migration Test [R. Moulias, J. M. Goust, A. Deville-Chabrolle, C. Buffet and C. N. Muller-Berat "Le test de migration des leucocytes (TML), un nouveau test d'hypersensibilite retardee in vitro chez i'homme" Presse. Med. 78, 2315 – 8 (1970)] or the Lymphocyte Transformation Test, to show that the transfer factor obtained by the process of the invention can induce an immune reaction in lymphocytes against the corresponding antigens. These results are confirmed by studies in vivo, wherein transfer factor produced by the process of the invention is injected into baboons, and their immune responses are subsequently studied. Humans have been treated against subacute sclerosing panencephalitis, systemic candidiasis, breast cancer, measles and chickenpox.

The results of these biological tests are confirmed by physico-chemical evaluation, e.g. as described in Example 7.

Production of transfer may be further enhanced by various methods. Since it has been observed that apparently not all cells in the lymphoblastoid cell population are good producers of transfer factor, those cells which do not produce transfer factor or which do not produce it well can be eliminated. The incubation of cells for short periods with mitostatic agents e.g. velbe, or incubation for a short period in the cold during the induction period apparently increases the amount of transfer factors produced, by selective killing of non-productive cells. Another alternative is the cloning of those cells which are found to be good producers. Alternatively, synchronization of a cell culture will enhance the production of transfer factors by allowing induction during a specific, more sensitive period of the cell cycle. In addition to humans and other primates, species of animals which can be treated with transfer factor produced according to the invention and whose cells can be used (after modification to produce lymphoblastoid cell lines) in culture to produce transfer factors include: bovines, ovines, equines, felines, canines an gallines.

Although certain preferred embodiments of the invention have been described, it will be readily apparent that many modifications thereto may be made by the man skilled in the art.

We claim:

1. A process for the in vitro production of transfer factor comprising:
    culturing in vitro at least one strain of lymphoblastoid cells in the presence of added transfer factor to propagate the cells and induce the production of transfer factor by them; and
    extracting the produced transfer factor.
2. The process of claim 1, wherein the produced transfer factor is extracted from the cultured lymphoblastoid cells.
3. The process of claim 1, wherein the produced transfer factor is extracted from a supernatant of the culture medium.

* * * * *